(12) United States Patent
Xu

(10) Patent No.: US 6,485,761 B1
(45) Date of Patent: Nov. 26, 2002

(54) METHODS FOR USING LACTONOHYDROLASES IN BAKING

(75) Inventor: Feng Xu, Woodland, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/511,964

(22) Filed: Feb. 24, 2000

Related U.S. Application Data

(63) Continuation-in-part of application No. 09/256,521, filed on Feb. 24, 1999, now abandoned.

(51) Int. Cl.[7] ................................................. A21D 8/04
(52) U.S. Cl. ........................... 426/18; 426/20; 426/555; 426/549
(58) Field of Search ................................ 435/196, 197; 426/18, 20, 21, 25, 28, 549, 555

(56) References Cited

U.S. PATENT DOCUMENTS

| | | | | |
|---|---|---|---|---|
| 2,783,150 A | * | 2/1957 | Luther | 99/93 |
| 4,990,343 A | * | 2/1991 | Haarasilta et al. | 426/10 |
| 5,082,786 A | * | 1/1992 | Nakamoto | 435/288 |
| 5,897,995 A | * | 4/1999 | Vroemen et al. | 435/137 |

FOREIGN PATENT DOCUMENTS

| | | |
|---|---|---|
| JP | WO 97/10341 | 3/1997 |

OTHER PUBLICATIONS

Shimizu et al., Jan. 1992, European Journal of Biochemistry 209: 383–390.
Shimizu & Kataoka, Jan. 1996, Annals of the New York Academy of Sciences 799: 650–658.
Kataoka et al., Jan. 1995, Applied Microbiology Biotechnology 44: 333–338.
Kataoka et al., Jan. 1996, Enzyme Microbiology Technology 19: 307–310.

\* cited by examiner

*Primary Examiner*—Keith Hendricks
(74) *Attorney, Agent, or Firm*—Robert L. Starnes

(57) ABSTRACT

The present invention relates to methods for preparing a dough, comprising incorporating into the dough a composition comprising an effective amount of one or more lactonohydrolases which improve one or more properties of the dough or a baked product obtained from the dough. The present invention also relates to methods for preparing a baked product. The present invention also relates to compositions comprising an effective amount of one or more lactonohydrolases for improving one or more properties of a dough and/or a baked product obtained from the dough. The present invention further relates to doughs or baked products and to pre-mixes for a dough.

20 Claims, 5 Drawing Sheets

```
CTCCCCACCACCACTCAGTTTCACTTCTACCTCATTGCCTTCCACCATTGCCCTTGTGTCGGGATTTGTGGC    80
                                          M  P  S  T  I  A  A  L  V  V  G  I  C  G

GTTGCCGCTGCCAAACTTCCCTCCACGGCTCAGGTCATTGATCAGAAGTCTTTCAATGTTTTGAAGGATGTCCCACCACC  160
 V  A  A  K  L  P  S  T  A  Q  V  I  D  Q  K  S  F  N  V  L  K  D  V  P  P  P

TTCCGTGGCTAATGACACACTGGTCTTTTACATGGCCCGGAGTGACAGAGGAATCTCTCGTCGAGAAACCCTTCCATGTTT  240
 S  V  A  N  D  T  L  V  F  T  W  P  G  V  T  E  E  S  L  V  E  K  P  F  H  V

ATGATGATGAATTCCTCGATGTCATCGGGAAAGGATCCCCTCTCTGACACTTGTTGCTACGTCAGAAAGCGACCCCATCTTC  320
 Y  D  D  E  F  L  D  V  I  G  K  D  P  S  L  T  L  V  A  T  S  E  S  D  P  I  F

CACGAGGCTGTAGTCTGGTACCCACCTACAGACGAGGTTTTTTTCGTGCAAAATGCGGAGCTCCTGCGGCAGGCACTGG    400
 H  E  A  V  V  W  Y  P  P  T  D  E  V  F  F  V  Q  N  A  G  A  P  A  A  G  T  G

CCTGAACAAGTCTTCCATCATCCAGAAGATTTCTCAAAGATGCAGAGGCTTTGCGCAAGGAACCCTAGGCAAGGATG      480
 L  N  K  S  S  I  I  Q  K  I  S  L  K  D  A  E  A  L  R  K  G  T  L  G  K  D

AAGTGAAGGTGACAGTCGTTGACACAGCTAACCCTCAAGTCATTAACCCCAATGTGGCATTTACTACAAGGGCGAAATC    560
 E  V  K  V  T  V  V  D  T  A  N  P  Q  V  I  N  P  N  G  G  I  Y  Y  K  G  E  I

ATCTTTGCTGGTGAAGGCCAAGGTGACGAAGTTCCCTGCCCTTTACCGGCCATGAACCCCTTGCCTCCATACAACACAAG   640
 I  F  A  G  E  G  Q  G  D  E  V  P  S  A  L  Y  R  M  N  P  L  P  P  Y  N  T  S
```

Fig. 1A

```
CACCCCTCCTCAACAACTACTTTGGCCGCCAGTTCAACTCCTTGAACGACGTTGGCATCAACCCCAGGAATGGTGACTTGT  720
 T  L  N  N  Y  F  G  R  Q  F  N  S  L  N  D  V  G  I  N  P  R  N  G  D  L

ACTTCACCGACACTCTCTACGGCTATCTCCAAGACTTCCGTCCCGTCCCTGTCTGCGAAACCAAGTGTACCGATACAAC  800
 Y  F  T  D  T  L  Y  G  Y  L  Q  D  F  R  P  V  P  G  L  R  N  Q  V  Y  R  Y  N

TTCGACACTGGTGCTGTGTAACTGTTGTGCTGATGACTTTACTCTTCCCAACGGTATTGGTTTTGCTCCTGATGGAAAGCG  880
 F  D  T  G  A  V  T  V  V  A  D  D  F  T  L  P  N  G  I  G  F  A  P  D  G  K  R

TGTCTATGTCACCGACACTGGCATCGCTCTCTTGGCTTCTACGGCCGTAACCTTTCCTCCCCCGCCCTCTGTTTACTCTTTCG  960
 V  Y  V  T  D  T  G  I  A  L  G  F  Y  G  R  N  L  S  S  P  A  S  V  Y  S  F

ACGTGAACAAGGATGGTACCCTTGAGAACCGCAAGACTTTTGCCTACGTAGCTTCTTTCATCCCAGACGGTGTTCATACC 1040
 D  V  N  K  D  G  T  L  E  N  R  K  T  F  A  Y  V  A  S  F  I  P  D  G  V  H  T

GATTCCAAGGGTCGTGTCGTATGCTGGTTGTGTGGTGACGGTGTCCATGTCTGGAACCCCTCTGGCAAGCTCATTGGCAAGAT 1120
 D  S  K  G  R  V  Y  A  G  C  G  D  D  G  V  H  V  W  N  P  S  G  K  L  I  G  K  I

CTATACCGGGATCACTGCTGCCAACTTCCAATTGCTGGAAAAGGAAGATTGATTATCACTGGTCAGACTAAGCTGTTCT 1200
 Y  T  G  I  T  A  A  N  F  Q  F  A  G  K  G  R  L  I  I  T  G  Q  T  K  L  F

ACGTTACCCTGGCTGCTTCAGGACCCAAGTTATATGACTAGAACTCCCCCTGTGGCAGTATAGAAACAGATATTTACCGT 1280
 Y  V  T  L  A  A  S  G  P  K  L  Y  D

ATTGATAGAAGATAATATTAATTATTAATCGATAAAAAAAAAAAAAAAAAAAA 1334
```

METHODS FOR USING LACTONOHYDROLASES IN BAKING

CROSS-REFERENCE TO RELATED APPLICATION

This application is a continuation-in-part of U.S. application Ser. No. 09/256,521 filed on Feb. 24, 1999, now abandoned which application is fully incorporated herein by reference.

BACKGROUND OF THE INVENTION

1. Field of the Invention

The present invention relates to methods for preparing a dough and/or baked product with a lactonohydrolase.

2. Description of the Related Art

The strength of a dough is an important aspect of baking for both small-scale and large-scale applications. A strong dough has a greater tolerance for mixing time, proofing time, and mechanical vibrations during dough transport, whereas a weak dough is less tolerant to these treatments. A strong dough with superior rheological and handling properties results from flour containing a strong gluten network. Flour with a low protein content or a poor gluten quality results in a weak dough.

Dough "conditioners" are well known in the baking industry. The addition of conditioners to bread dough has resulted in improved machinability of the dough and improved texture, volume, flavor, and freshness (anti-staling) of the bread. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough. However, the use of several of the currently available chemical oxidizing agents has been met with consumer resistance or is not permitted by regulatory agencies.

The use of enzymes as dough conditioners has been considered as an alternative to the chemical conditioners. A number of enzymes have been used recently as dough and/or bread improving agents, in particular, enzymes that act on components present in large amounts in the dough. Examples of such enzymes are found within the groups of amylases, proteases, glucose oxidases, and (hemi)cellulases, including pentosanases.

Lactonohydrolases reversibly catalyze the hydrolysis of lactone compounds to hydroxy acids, i.e., they mediate the interconversion between the lactone and acid forms of hydroxy carboxylic acids.

Shimizu et al. (1992, *European Journal of Biochemistry* 209: 383–390) have disclosed a lactonohydrolase obtained from *Fusarium oxysporum*. This enzyme preparation stereospecifically hydrolyzes aldonate lactones such as D-galactono-γ-lactone and D-glucono-δ-lactone. In addition, the *Fusarium oxysporum* lactonohydrolase catalyzes the asymmetric hydrolysis of D-pantoyl lactone, which can be used as a chiral building block for the synthesis of D-pantothenate (Shimazu and Kataoka, 1996, *Annals of the New York Academy of Sciences* 799:650–658; Kataoka et al., 1995, *Appl. Microbiol. Biotechnol.* 44: 333–338; Kataoka et al., 1996, *Enzyme Microb. Technol.* 19: 307–310). Furthermore, lactonohydrolase irreversibly hydrolyzes a number of aromatic lactones, such as dihydrocoumarin and homogentisic-acid lactone.

The cloning and expression of a *Fusarium oxysporum* lactonohydrolase gene has been disclosed (WO 97/10341).

It is the object of the present invention to improve the properties of dough and/or baked products by the use of a lactonohydrolase.

SUMMARY OF THE INVENTION

The present invention relates to methods for preparing a dough, comprising incorporating into the dough an effective amount of one or more lactonohydrolases.

The present invention also relates to methods for preparing a baked product.

The present invention also relates to compositions comprising an effective amount of one or more lactonohydrolases, for improving one or more properties of a dough and/or a baked product obtained from the dough, and a carrier and/or a baking ingredient.

The present invention also relates to doughs or baked products.

The present invention further relates to pre-mixes for a dough comprising an effective amount of one or more lactonohydrolases, for improving one or more properties of a dough and/or a baked product obtained from the dough, and a carrier and/or a baking ingredient.

BRIEF DESCRIPTION OF THE FIGURES

FIGS. 1A and 1B show the cDNA sequence and the deduced amino acid sequence of a *Fusarium venenatum* lactonohydrolase (SEQ ID NOS. 1 and 2, respectively).

DETAILED DESCRIPTION OF THE INVENTION

Figure 2:
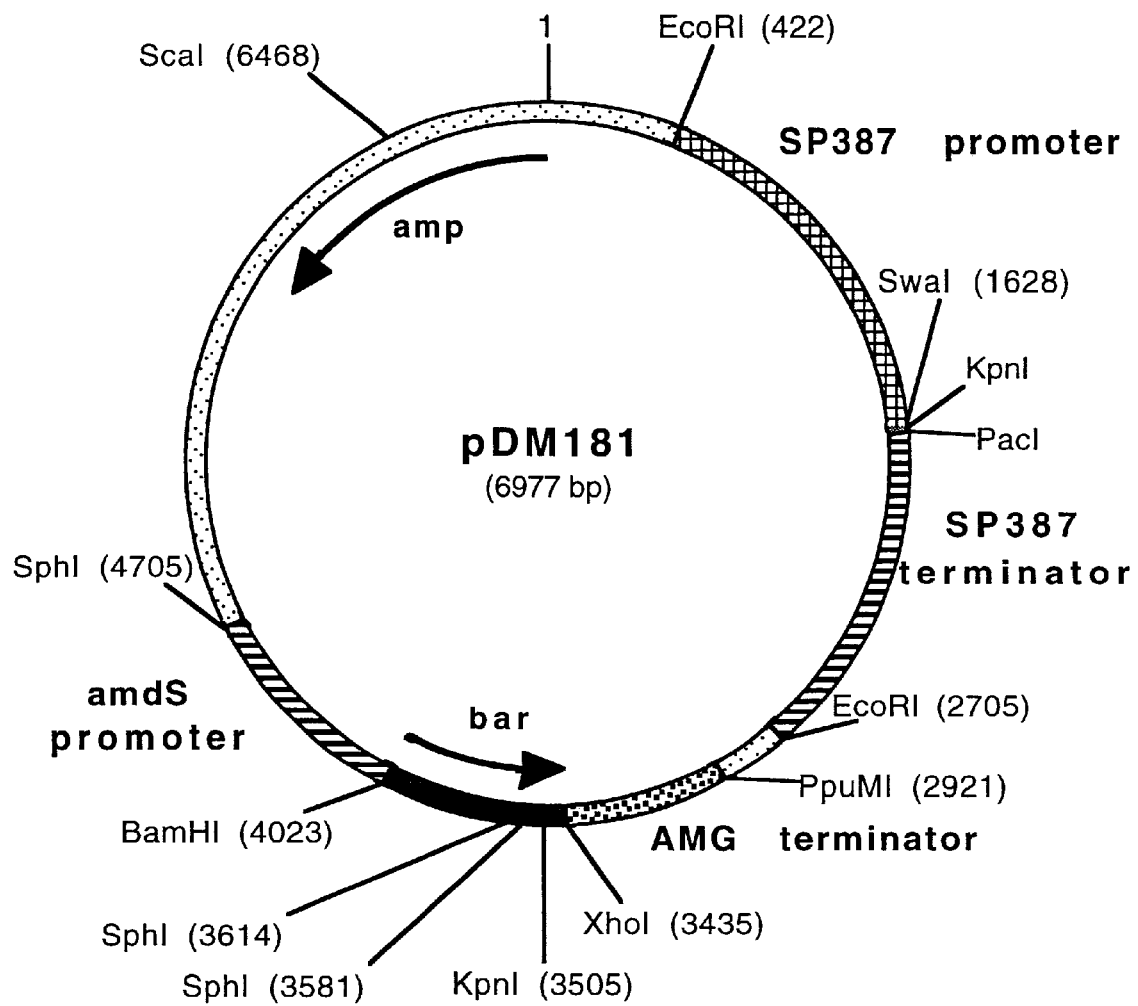
FIG. 2 shows a restriction map of pDM181.

The present invention relates to methods for preparing a dough or a baked product comprising incorporating into the dough an effective amount of one or more lactonohydrolases which improve one or more properties of the dough or the baked product obtained from the dough relative to a dough or a baked product in which a lactonohydrolase is not incorporated.

In the methods of the present invention, one or more lactonohydrolases are incorporated into the dough by adding the lactonohydrolase(s) to the dough, to any single ingredient from which the dough is to be made, and/or to any mixture of dough ingredients from which the dough is to be made. In other words, the lactonohydrolase(s) may be added in any step of the dough preparation and may be added in one, two, or more steps.

The term "lactonohydrolase" is defined herein as a hydrolase which catalyzes the hydrolysis of aldonate and aromatic lactones to the corresponding aldonic acids. For purposes of the present invention, lactonohydrolase activity is determined according to the procedure described by Shimizu et al., 1992, *European Journal of Biochemistry* 209: 383–390, where the hydrolysis of D-galactono-γ-lactone is measured.

The term "effective amount" is defined herein as an amount of a lactonohydrolase that is sufficient for providing a measurable effect on at least one property of interest of the dough and/or baked product.

The term "improved property" is defined herein as any property of a dough and/or a product obtained from the dough, particularly a baked product, which facilitates dough handling and/or production of a more desirable final product, by the action of a lactonohydrolase relative to a dough or product in which a lactonohydrolase is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The use of a lactonohydrolase may result in an increased strength, stability, and/or reduced stickiness of the dough, resulting in improved machinability, as well as in an increased volume and improved crumb structure and softness of the baked product. The effect on the dough may be particularly advantageous when a poor quality flour is used. Improved machinability is of particular importance in connection with dough that is to be processed industrially.

The improved property may be determined by comparison of a dough and/or a baked product prepared with and without addition of a lactonohydrolase in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated as mentioned above by a trained test panel.

The term "improved antistaling of the baked product" is defined herein as the properties of a baked product that have a reduced rate of deterioration of quality parameters, e.g., softness and/or elasticity, during storage.

In a preferred embodiment, the one or more lactonohydrolases improve one or more properties of the dough or the baked product obtained from the dough. In another preferred embodiment, the one or more lactonohydrolases improve one or more properties of the dough and the baked product obtained from the dough.

In a preferred embodiment, the improved property is increased strength of the dough. In another preferred embodiment, the improved property is increased elasticity of the dough. In another preferred embodiment, the improved property is increased stability of the dough. In another preferred embodiment, the improved property is reduced stickiness of the dough. In another preferred embodiment, the improved property is improved extensibility of the dough. In another preferred embodiment, the improved property is improved machinability of the dough. In another preferred embodiment, the improved property is increased volume of the baked product. In another preferred embodiment, the improved property is improved crumb structure of the baked product. In another preferred embodiment, the improved property is improved softness of the baked product. In another preferred embodiment, the improved property is improved flavor of the baked product. In another preferred embodiment, the improved property is improved antistaling of the baked product.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters*.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

The lactonohydrolase(s) may be any lactonohydrolase which provides an improved property to a dough and/or to a baked product obtained from the dough.

Examples of lactonohydrolases useful in the methods of the present inventions are defined by the Nomenclature Committee of the International Union of Biochemistry on the Nomenclature and Classification of Enzymes and listed as enzyme subclasses E.C. 3.1.1.-.

In the methods of the present invention, any lactonohydrolase may be used which possesses suitable enzyme activity in a pH and temperature range appropriate for making a dough and/or a baked product. It is preferable that the lactonohydrolase(s) is active over broad pH and temperature ranges.

In a preferred embodiment, the lactonohydrolase(s) has a pH optimum in the range of about 3 to about 10. In a more preferred embodiment, the lactonohydrolase(s) has a pH optimum in the range of about 4.5 to about 8.5.

In another preferred embodiment, the lactonohydrolase(s) has a temperature optimum in the range of about 5° C. to about 100° C. In a more preferred embodiment, the lactonohydrolase(s) has a temperature optimum in the range of about 25° C. to about 75° C.

In another preferred embodiment, the lactonohydrolase is an L-arabinonolactonase (E.C. 3.1.1.15), D-gluconolactonase (E.C. 3.1.1.17), D-glucuronolactonase (E.C. 3.1.1.19), 3-oxoadipate enol-lactonase (E.C. 3.1.1.24), 1,4-lactonase (E.C. 3.1.1.25), D-arabinolactonase (E.C. 3.1.1.30), or 6-phosphogluconolactonase (E.C. 3.1.1.31).

In the methods of the present invention, combinations of lactonohydrolases may be used to improve one or more properties of the dough and/or baked product obtained from the dough.

The source of a lactonohydrolase is not critical for improving one or more properties of a dough and/or a baked product. Accordingly, the lactonohydrolase(s) may be obtained from any source such as a plant, microorganism, or animal. The lactonohydrolase(s) is preferably obtained, e.g., from a microbial source, such as a bacterium or a fungus, e.g., a filamentous fungus or a yeast.

In a preferred embodiment, the lactonohydrolase(s) is obtained from a bacterial source. For example, the lactonohydrolase(s) may be obtained from an Acetobacter, Acinetobacter, Agrobacterium, Alcaligenes, Arthrobacter, Azotobacter, Bacillus, Comamonas, Clostridium, Gluconobacter, Halobacterium, Mycobacterium, Rhizobium, Salmonella, Serratia, Streptomyces, *E. coli*, Pseudomonas, Wolinella, or methylotrophic bacterium strain.

In a more preferred embodiment, the lactonohydrolase(s) is obtained from an *Acetobacter aceti, Alcaligenes faecalis, Arthrobacter oxidans, Azotobacter vinelandii, Bacillus alkalophilus, Bacillus amyloliquefaciens, Bacillus anitratum, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Comamonas testosteroni, Clostridum tyrobutyricum, Gluconobacter dioxyaceticus, Gluconobacter liquefaciens, Gluconobacter suboxydans, Halobacterium cutirubrum, Mycobacterium convolutum, Rhizobium melioti, Salmonella typhimurium, Serratia marcescens, Streptomyces lividans, Streptomyces murinus, Pseudomonas aeruginosa, Pseudomonas fluorescens, Pseudomonas putida,* or *Wolinella succinogens* strain.

In another preferred embodiment, the lactonohydrolase(s) is obtained from a fungal source. For example, the lactonohydrolase(s) may be obtained from a yeast strain such as a Candida, Kluyveromyces, Pichia, Saccharomyces, Schizosaccharomyces, or Yarrowia strain; or from a filamentous fungal strain such as an Acremonium, Aspergillus, Aureobasidium, Chrysosporium, Cryptococcus, Filibasidium, Fusarium, Humicola, Magnaporthe, Monilia, Mucor, Myceliophthora, Neocallimastix, Neurospora, Paecilomyces, Penicillium, Phanerochaete, Piromyces, Schizophyllum, Sclerotium, Sporotrichum, Talaromyces, Thermoascus, Thielavia, Tolypocladium, or Trichoderma strain.

In another more preferred embodiment, the lactonohydrolase(s) is obtained from a *Saccharomyces carisbergensis, Saccharomyces cerevisiae, Saccharomyces diastaticus, Saccharomyces douglasii, Saccharomyces kluyveri, Saccharomyces norbensis,* or *Saccharomyces oviformis* strain.

In another more preferred embodiment, the lactonohydrolase(s) is obtained from an *Aspergillus aculeatus, Aspergillus awamori, Aspergillus foetidus, Aspergillus japonicus, Aspergillus nidulans, Aspergillus niger, Aspergillus oryzae, Chrysosporium lignorum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, Fusarium venenatum, Humicola insolens, Humicola lanuginosa, Monilia sitophila, Mucor miehei, Myceliophthora thermophila, Neurospora crassa, Penicillium purpurogenum, Phanerochaete chrysporum, Polyporus pinsitus, Polyporus versicolor, Sclerotium rolfsii, Sporotrichum thermophile, Trichoderma citrinoviride, Trichoderma hamatum, Trichoderma harzianum, Trichoderma koningii, Trichoderma longibrachiatum, Trichoderma polysporum, Trichoderma reesei, Trichoderma saturnisporum,* or *Trichoderma viride* strain.

In a most preferred embodiment, the lactonohydrolase is obtained from *Fusarium venenatum* or *Fusarium oxysporum*. In another most preferred embodiment, the L-arabinonolactonase is obtained from *Azospirillium brasilense*. In another most preferred embodiment, the D-gluconolactonase is obtained from *Saccharomyces cerevisiae, E. coli, Zymomonas mobilis,* or pig. In another most preferred embodiment, the 3-oxoadipate enol-lactonase is obtained from *Rhodococcus erythropolis, Ralstonia eutropa (Alcaligenes eutrophus)*,or *Psudomonas cepacia*. In another most preferred embodiment, the 1,4-lactonase is obtained from *Acinetobacter calcoaceticus* or *Psudomonas putida*. In another most preferred embodiment, the D-arabinolactonase is obtained from *Pseudomaonas saccharophila*. In another most preferred embodiment, the 6-phosphogluconolactonase is obtained from *Saccharomyces cerevisiae* or *Zymomonas mobilis*.

The lactonohydrolase(s) may be obtained from the organism in question by any suitable technique, and in particular by use of recombinant DNA techniques known in the art (c.f. Sambrook, J. et al., 1989, *Molecular Cloning, A Laboratory Manual,* Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA or synthetic origin or any mixture of these, and may be isolated or synthesized in accordance with methods known in the art. The enzyme may also be obtained from its naturally occurring source, such as a plant or organism, or relevant part thereof. Furthermore, the lactonohydrolase(s) may be obtained from commercial suppliers.

When a lactonohydrolase is added to dough intended for use in the preparation of baked products, the enzyme may exert its effect by catalyzing the hydrolysis of a lactone to carboxyl groups thereby increasing the charge distribution and hydrophilicity in the dough which affects a variety of physicochemical properties such as water adsorption and interactions among starch, pentosan, gluten, lipids, etc. The lactonohydrolase(s) is used in an amount sufficient to provide the desired effect, i.e., the improved properties in question. Thus, the dosage of the lactonohydrolase(s) to be used in the methods of the present invention should be adapted to the nature and composition of the dough in question as well as to the nature of the lactonohydrolase(s) to be used.

The term "composition" is defined herein as a dough-improving and/or baked product-improving composition which, in addition to one or more lactonohydrolases, comprise one or more additional substances conventionally used in baking. The additional substance(s) may be other enzymes or chemical additives known in the art to be useful in dough preparation and/or baking.

The bread-improving and/or dough improving composition of the invention is generally included in the dough in an amount corresponding to 0.01–5%, in particular 0.1–3%. The lactonohydrolase(s) is typically added in an amount corresponding to 0.01–100 mg enzyme protein per kg of flour, preferably 0.1–25 mg enzyme protein per kg of flour, more preferably 0.1–10 mg enzyme protein per kg of flour, and most preferably 0.5–5 mg enzyme protein per kg of flour.

In terms of enzyme activity, the appropriate dosage of a given lactonohydrolase for exerting a desirable improvement of dough and/or baked products will depend on the enzyme and the enzyme substrate in question. The skilled person may determine a suitable enzyme unit dosage on the basis of methods known in the art.

The lactonohydrolase(s) and/or additional enzymes to be used in the methods of the present invention may be in any form suitable for the use in question, e.g., in the form of a dry powder, agglomerated powder, or granulate, in particular a non-dusting granulate, a liquid, in particular a stabilized liquid, or a protected enzyme. Granulates and agglomerated powders may be prepared by conventional methods, e.g., by spraying the lactonohydrolase(s) onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy. The lactonohydrolase(s) and/or additional enzymes may be contained in slow-release formulations. Methods for preparing slow-release formulations are well known in the art. Liquid enzyme preparations may, for instance, be stabilized by adding nutritionally acceptable stabilizers such as a sugar, a sugar alcohol or another polyol, and/or lactic acid or another organic acid according to established methods.

For inclusion in pre-mixes or flour it is advantageous that the lactonohydrolase(s) is in the form of a dry product, e.g., a non-dusting granulate, whereas for inclusion together with a liquid it is advantageously in a liquid form.

A substrate of the lactonohydrolase in question may also be incorporated into the dough. The substrate may be incorporated into dough separately or together with the lactonohydrolase of interest, optionally as constituent(s) of the bread-improving and/or dough-improving composition.

A preferred substrate for an L-arabinonolactonase (E.C. 3.1.1.15) is L-arabinono-1,4-lactone. A preferred substrate for a D-gluconolactonase (E.C. 3.1.1.17) is D-glucono-1,5-lactone. A preferred substrate for a D-glucuronolactonase (E.C. 3.1.1.19) is D-glucurono-6,2-lactone. A preferred substrate for 3-oxoadipate enol-lactonase (E.C. 3.1.1.24) is 3-oxoadipate enol-lactone. A preferred substrate for a 1,4-lactonase (E.C. 3.1.1.25) is a 1,4-lactone, e.g., gamma-butyrolactone, gamma-valerolactone, gamma-caprolactone, gamma-octalactone, etc. A preferred substrate for a D-arabinonolactonase (E.C. 3.1.1.30) is D-arabinono-1,4-lactone. A preferred substrate for a 6-phosphogluconolactonase (E.C. 3.1.1.31) is 6-phospho-D-glucono-1,5-lactone. Other substrates for these lactonohydrolases are described in D. Schomburg and M. Salzmann, editors, 1991, *Enzyme Handbook 3*, Springer-Verlag, New York.

Alternatively, an enzyme which acts on a substance endogenous to the flour to produce a substrate for the lactonohydrolase of interest may also be incorporated in the dough. Furthermore, the substance and the enzyme which acts on the substance to produce a substrate for the lactonohydrolase of interest may also be incorporated in the dough. For example, various carbohydrate oxidases, e.g., glucose oxidase, may be used to convert L-arabinose to L-arabinono-1,4-lactone, which then may serve as a substrate for L-arabinonolactonase; or to convert D-glucose to D-glucono-1,5-lactone, which then may serve as a substrate for D-gluconolactonase.

The specific amount of the substrate available for the lactonohydrolase of interest will depend on a number of factors, such as the baking process used, the length of time for mixing, fermentation, proofing and/or baking, the quality of the yeast and/or flour used, as well as the activity of endogenous and exogenous enzymes present.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling), a beta-amylase, a cyclodextrin glucanotransferase, a peptidase, in particular, an exopeptidase (useful in flavour enhancement), a transglutaminase, a lipase (useful for the modification of lipids present in the dough or dough constituents so as to soften the dough), a phospholipase (useful for the modification of lipids present in the dough or dough constituents so as to soften the dough and improve gas retention in the dough), a cellulase, a hemicellulase, in particular a pentosanase such as xylanase (useful for the partial hydrolysis of pentosans which increases the extensibility of the dough), a protease (useful for gluten weakening in particular when using hard wheat flour), a protein disulfide isomerase, e.g., a protein disulfide isomerase as disclosed in WO 95/00636, a glycosyltransferase, a peroxidase (useful for improving the dough consistency), a laccase, or an oxidase, e.g., an aldose oxidase, a glucose oxidase, a pyranose oxidase, a lipoxygenase, or an L-amino acid oxidase (useful in improving dough consistency).

The xylanase is preferably of microbial origin, e.g., derived from a bacterium or fungus, such as a strain of Aspergillus, in particular *Aspergillus aculeatus, Aspergillus niger* (cf. WO 91/19782), *Aspergillus awamori* (WO 91/18977), or *Aspergillus tubigensis* (WO 92/01793), from a strain of Trichoderma, e.g., *Trichoderma reesei*, or from a strain of Humicola, e.g., *Humicola insolens* (WO 92/17573, the contents of which is hereby incorporated by reference).

Commercially available amylases useful in the present invention are NOVAMYL™ (a *Bacillus stearothermophilus* maltogenic amylase, available from Novo Nordisk A/S, Denmark), FUNGAMYL® (an *Aspergillus oryzae* alpha-amylase, available from Novo Nordisk A/S, Denmark), and BAN™ (a *Bacillus licheniformis* alpha-amylase, available from Novo Nordisk A/S, Denmark). A commercially available amyloglucosidase is AMG™ (an *Aspergillus niger* amyloglucosidase, available from Novo Nordisk A/S, Denmark). Other useful commercially available amylase products include GRINDAMYL™ A 1000 or A 5000 (available from Grindsted Products, Denmark) and AMYLASE H or AMYLASE P (available from Gist-Brocades, The Netherlands). A commercially available glucose oxidase is GLUZYME™ (an *Aspergillus niger* glucose oxidase, available from Novo Nordisk A/S, Denmark). Commercially available proteases are NEUTRASE™ (a *Bacillus amyloliquefaciens* endoprotease, available from Novo Nordisk A/S, Denmark) and GLUTENASE™ (available from Novo Nordisk A/S, Denmark). Commercially available pentosanases are PENTOPAN™ (a *Humicola insolens* pentosanase, available from Novo Nordisk A/S, Denmark) and PENTOPAN™ MONO (a *Thermomyces lanuginosus* pentosanase, available from Novo Nordisk A/S, Denmark). A commercially available lipase is NOVOZYM® 677 BG (a *Thermomyces lanuginosus* lipase, available from Novo Nordisk A/S, Denmark).

When one or more additional enzyme activities are to be added in accordance with the methods of the present invention, these activities may be added separately or together with the lactonohydrolase(s), optionally as constituent(s) of the bread-improving and/or dough-improving composition. The other enzyme activities may be any of the enzymes described above and may be dosed in accordance with established baking practices.

In addition to the above-mentioned additional enzymes, a lactonohydrolase may contain varying minor amounts of other enzymatic activities inherently produced by the producer organism in question.

In addition, or as an alternative, to additional enzyme components, a conventionally used baking agent may also be incorporated into the dough. The baking agent may include proteins, such as milk powder (to provide crust colour), gluten (to improve the gas retention power of weak flours), and soy (to provide additional nutrients and improve water binding); eggs such (either whole eggs, egg yolks or egg whites); fat such as granulated fat or shortening (to soften the dough and improve the texture of the bread); emulsifier (to improve dough extensibility and, to some extent, the consistency of the resulting bread); oxidant, e.g., ascorbic acid, potassium bromate, potassium iodate, azodicarbon amide (ADA) or ammonium persulfate (to strengthen the gluten structure); amino acid, e.g., L-cysteine (to improve mixing properties); sugar; salt, e.g., sodium chloride, calcium acetate, sodium sulfate or calcium sulphate (to make the dough firmer); flour; and starch. Such components may also be added to the dough in accordance with the methods of the present invention.

Examples of suitable emulsifiers are mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, and lecithin.

The dough and/or baked product may be based on wheat meal or flour, optionally in combination with other types of meal or flour such as corn meal, corn flour, rye meal, rye flour, oat meal, oat flour, soy meal, soy flour, sorghum meal, sorghum flour, potato meal, or potato flour.

The handling of the dough may be performed in any suitable manner, typically including the steps of kneading the dough, subjecting the dough to one or more proofing treatments, and baking the product under suitable conditions, i.e., at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

The dough of the invention is generally a leavened dough or a dough to be subjected to leavening. The dough may be leavened in various ways such as by adding sodium bicarbonate or the like, or by adding a leaven (fermenting dough), but it is preferable that the dough be leavened by adding a suitable yeast culture, such as a culture of *Saccharomyces cerevisiae* (baker's yeast). Any of the commercially available *Saccharomyces cerevisiae* strains may be employed.

The present invention also relates to the use of a lactonohydrolase for the preparation of pasta dough, preferably prepared from durum flour or a flour of comparable quality. The dough may be prepared by use of conventional techniques and the lactonohydrolase(s) used in a similar dosage as that described above. The lactonohydrolase(s) may be any of the types described above. When used in the preparation of pasta, the lactonohydrolase(s) results in a strengthening of the gluten structure, a reduction in the dough stickiness, and increased dough strength.

The present invention also relates to methods for preparing a baked product, comprising baking a dough obtained by a method of the present invention to produce a baked product. The baking of the dough to produce a baked product may be performed using methods well known in the art.

The present invention also relates to compositions comprising an effective amount of one or more lactonohydrolases and a carrier and/or a baking ingredient. The compositions may further comprise a substrate for the lactonohydrolase(s), one or more additional enzymes, one or more conventionally used baking agents, an enzyme which acts on a substance endogenous to the flour to produce a substrate for the lactonohydrolase(s) of interest, and/or a substance and the enzyme which acts on the substance to produce a substrate for the lactonohydrolase(s).

The present invention also relates to doughs and baked products, respectively, produced by the methods of the present invention.

The present invention further relates to a pre-mix, e.g., in the form of a flour composition, for dough and/or baked products made from dough, in which the pre-mix comprises a lactonohydrolase. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing a lactonohydrolase or a bread-improving and/or dough-improving composition of the invention comprising a lactonohydrolase with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise the lactonohydrolase(s). The baking additive preferably has a narrow particle size distribution with more than 95% (by weight) of the particles in the range from 25 to 500 $\mu$m.

The present invention is further described by the following examples that should not be construed as limiting the scope of the invention.

EXAMPLES

Materials and Methods

Preparation of White Bread (I)

The straight-dough bread-making method may be used according to AACC Method 10-10B (in Approved Methods of the American Association of Cereal Chemists, Ninth Edition, March 1995; AACC, St. Paul Minn., USA).

| Basic recipe | |
|---|---|
| Wheat flour | 100% |
| Salt | 1.5% |
| Yeast (fresh) | 5.3% |
| Sugar | 6.0% |
| Shortening | 3.0% |
| Water | optimum |

All percentages are by weight relative to the wheat flour.
Procedure
1. Dough mixing (Hobart mixer):
   The mixing time and speed should be determined by the skilled baker so as to obtain an optimum dough consistency under the testing conditions used.
2. 1st punch (e.g. 52 minutes after start)
3. 2nd punch (e.g., 25 minutes later)
4. Molding and panning (e.g., 13 minutes later).
5. Proofing to desired height (e.g., 33 minutes at 32° C., 82% RH)
6. Baking (e.g., at 215° C. for 24 minutes)

Preparation of White Bread (II)

The sponge-dough bread-making method may be used according to AACC Method 10-11 (in Approved Methods of the American Association of Cereal Chemists, Ninth Edition, March 1995; AACC, St. Paul Minn., USA).

| Basic recipe for Sponge | |
|---|---|
| Wheat flour | 60% |
| Yeast (compressed) | 36% |
| Yeast Food | 2% |
| Water | 36% |

All percentages are by weight relative to the wheat flour.
Procedure
1. Add water to compressed yeast
2. Add yeast food in dry form with flour
3. Mix sponge (Hobart A-120; Hobart Corp., Troy Ohio, USA):
   0.5 minute at $1^{st}$ speed
   1 minute at $2^{nd}$ speed
   The mixing time may be adjusted so as to obtain an optimum dough consistency under the testing conditions used.
4. Ferment in a fermentation cabinet: 4 hours at 30° C., 85% RH

| Basic recipe for Dough | |
|---|---|
| Wheat flour | 40% |
| Water | 24% |
| Sugar | 5% |
| Shortening | 3% |
| Salt | 2% |

All percentages are by weight relative to the wheat flour.
Procedure
1. Add dough ingredients; begin mixer ($1^{st}$ speed)
2. Add sponge in three approximately equal portions at 15, 25, and 35 seconds mixing time; total mixing time: 1 minute
3. At $2^{nd}$ speed, mix to obtain an optimum dough consistency
4. Ferment in a fermentation cabinet: 30 minutes at 30° C., 85% RH
5. Intermediate proof: 12–15 minutes in fermentation cabinet
6. Mold and final proof at 35.5° C., 92% RH
7. Bake: 25 minutes at 218° C.

Evaluation of Staling Properties of Bread

The degree of staling is determined on bread, e.g., on day 1, 3, 7 and 9 after baking. Evaluation of staleness and texture can be done according to AACC method 74-09. The principles for determination of softness and elasticity of bread crumb are as follows:
1. A slice of bread is compressed with a constant speed in a texture analyser, measuring the force for compression in g.
2. The softness of the crumb is measured as the force at 25% compression.
3. The force at 40% compression (P2) and after keeping 40% compression constant for 30 seconds (P3) is measured. The ratio (P3/P2) is the elasticity of the crumb.

Preparation of White Layer Cake

The method may be used according to AACC Method 10-90 (in Approved Methods of the American Association of Cereal Chemists, Ninth Edition, March 1995; AACC, St. Paul Minn., USA).

| Basic recipe | |
|---|---|
| Flour | 100% |
| Sugar | 140% |
| Shortening | 50% |
| Nonfat Dry Milk | 12% |
| Dried Egg Whites | 9% |
| Salt | 3% |
| Baking Powder and Water | determined empirically |

All percentages are by weight relative to the flour.
Procedure
1. Combine all dry ingredients and sift well
2. Add shortening and 60% of water
3. Mix at low speed for 0.5 minute in Hobart C-100 mixer
4. Mix at medium speed for 4 minutes
5. Add 50% of remaining water
6. Mix at low speed for 0.5 minute, scrape down and mix at medium speed for 2 minutes
7. Add remaining water, mix at low speed for 0.5 minute, scrape down and mix at medium speed for 2 minutes
8. Scale batter into each of two greased pans
9. Bake at 375° C. or 350° C.

Evaluation of Cakes

Cakes should be graded for volume and texture on the same day as baked according to AACC Method 10-90.

The internal structure may be scored for the uniformity and size of cells as well as thickness of the walls; the grain; texture, such as moisture, tenderness and softness; crumb colour; and flavour.

Preparation of Cookies

Cookies may be prepared according to AACC Method 10-50D (in Approved Methods of the American Association of Cereal Chemists, Ninth Edition, March 1995; AACC, St. Paul Minn., USA).

| Basic recipe | |
|---|---|
| Flour | 225 g |
| Water | 16 g |
| Dextrose Solution | 33 g |
| Bicarbonate of Soda | 2.5 g |
| Salt | 2.1 g |
| Sugar | 130 g |
| Shortening | 64 g |

Procedure
1. Cream shortening, sugar, salt and soda on low speed 3 minutes using an electric mixer (e.g., Hobart C-100)
2. Add dextrose solution and distilled water
3. Mix at low speed for 1 minute
4. Mix at medium speed for 1 minute
5. Add all flour and mix at low speed for 2 minutes
6. Scrape dough from bowl and place six portions at well-spaced points on lightly greased cookie sheet
7. Flatten dough lightly
8. Cut dough with cookie cutter
9. Bake at 205° C. for 10 minutes Evaluation of Cookies Cookie width should be measured after cooling 30 minutes and can be done by the method according to AACC Method 10-50D.

The width of each of the six cookies is measured in mm, then rotated 90° and remeasured to obtain the average width (W). An average thickness (T) may be obtained by measuring the cookies stacked on top of one another, then restacked in a different order. The spread factor is the ratio of W/T. However, the most sensitive and reliable estimate is the width measurement, and in some cases, thickness. Because the spread factor is a ratio of 2 empirically determined parameters, different values of W and T can result in the same W/T.

Preparation of Biscuits

Biscuits may be prepared according to AACC Method 10-31B (in Approved Methods of the American Association of Cereal Chemists, Ninth Edition, March 1995; AACC, St. Paul Minn., USA).

| Basic recipe | |
|---|---|
| Flour | 228 g |
| Shortening | 40 g |
| Milk Solution[1] | 135 g |
| Bicarbonate of Soda[2] | 3.4 g |
| Salt[2] | 4.5 g |
| Monocalcium Phosphate[2] | 130 g |

[1] 50 g milk powder in 450 ml water
[2] omit if self-rising flour is used; use 240 g of self-rising flour Procedure
1. Sift together flour and other dry ingredients (bicarbonate of soda, salt and monocalcium phosphate, if used)
2. Add shortening to flour mixture
3. Mix, using electric mixer (e.g., Hobart, Kitchen Aid or equivalent) with timer control, at speed 1 for 15 seconds
4. Mix at speed 1 for 3 minutes
5. Add milk solution and mix at speed 1 for 15 seconds
6. Roll out dough using floured rolling pin
7. Cut dough with floured cutter
8. Place 8 dough pieces 4 cm apart on ungreased baking sheet.
9. Bake at 232° C. for 10 minutes Evaluation of Biscuits Upon removal from oven, biscuits should be removed from the baking sheet and cooled for 30 minutes. Measurements of the eight biscuits can be made according to AACC Method 10-31B to obtain a total weight, a total diameter and a height at the top center of each biscuit.

Preparation of Pie Shells

Pie shells may be prepared according to AACC Method 10-60 (in Approved Methods of the American Association of Cereal Chemists, Ninth Edition, March 1995; AACC, St. Paul Minn., USA).

| Basic recipe | |
|---|---|
| Flour | 100% |
| Shortening | 60% |
| Salt | 3.5% |
| Water | 30–64% |

All percentages are by weight relative to the wheat flour, and all ingredients are at 10° C. before mixing.

Procedure
1. Sift flour twice
2. Add shortening to flour and cut for 5 minutes using electric mixer (e.g., Hobart, Kitchen Aid or equivalent) with timer control, on low speed
3. Dissolve salt in a portion of water
4. Add salt solution to flour-shortening mixture, together with additional water if necessary
5. Mix at low speed for 2 minutes
6. Store dough at 10° C. for 24 hours Empty shells
7. Scale, press dough into ball
8. Roll dough, fold and roll again
9. Fold and roll a third time
10. Lay dough sheet over an inverted pie tin
11. Trim dough and prick with fork
12. Let dry for 30 minutes and cover with a second pan pressed down firmly
13. Bake at 218° C. for 20–25 minutes, removing second pan after 10 minutes in the oven Filled Pies
7. Scale and roll bottom crust as outlined above for empty pie shell
8. Press dough sheet into pie tin and fill with either artificial fruit acid filling (water, corn starch, sugar and citric acid crystals) or true fruit filling (cling peaches, sugar corn starch and water)
9. Scale and roll dough once for top crust
10. Place over filling, trim and cut center lightly
11. Press edge over wetted edge of bottom crust
12. Bake at 218° C. for about 30 minutes Evaluation of Pie Crusts Viscosity may be evaluated according to AACC Method 56-80. Other parameters of empty and filled pie shells may be measured according to AACC Method 10-60 24 hours and 12 or 16 hours after baking, respectively, Pie crusts may be evaluated empirically for whether they are baked through; the edges have shrunk from edge of pan; blisters have appeared; the texture is flaky; the mouth-feel is tender; whether they are crisp or soft; the colour; and if the fruit filling has penetrated the crust.

Testing of Doughs and Breads

The effect of adding a lactonohydrolase may be tested in doughs and breads by using the following method:

| Recipe: | |
|---|---|
| Water | 60% |
| Wheat Flour | 100% |
| Yeast | 4% |
| Salt | 1.5% |
| Sugar | 1.5% |

The wheat flour is of the type Meneba 964.
Preparation of Breads
Procedure
1. Dough mixing (Spiral mixer)
   3 minutes at low speed
   8 minutes at high speed
   The mixing time may be adjusted by the skilled baker to obtain an optimum dough consistency under the testing conditions used.
2. 1st proof: 30° C.—80% RH, 20 minutes
3. Scaling and shaping;
4. Final proof: 32° C.—80% RH, 40 minutes;
5. Baking: 225° C., 20 minutes for rolls and 30 minutes for loaf.

Evaluation of Dough and Baked Products

Dough and baked products made from the straight dough method described above may be evaluated as follows for loaf specific volume, dough stickiness, dough firmness, dough extensibility, dough elasticity, crumb structure, and gluten strength.

Loaf specific volume: The mean value of 4 loaves volume are measured using the traditional rape seed method. The specific volume is calculated as volume ml per g bread. The specific volume of the control (without enzyme) is defined as 100. The relative specific volume index is calculated as:

$$\text{Specific vol. index} = \frac{\text{specific vol. of 4 loaves}}{\text{spec. vol. of 4 control loaves}} \times 100$$

The dough stickiness, firmness, extensibility, elasticity and crumb structure may be evaluated relative to controls by the skilled test baker according to the following scale:

| Dough stickiness: | almost liquid | 1 |
|---|---|---|
| | too sticky | 2 |
| | sticky | 3 |
| | normal | 4 |
| | dry | 5 |
| | too dry | 6 |
| Crumb structure: | very poor | 1 |
| | poor | 2 |
| | non-uniform | 3 |
| | uniform/good | 4 |
| | very good | 5 |
| Dough Firmness: | extremely soft | 1 |
| | too soft | 2 |
| | soft/good | 3 |
| | normal | 4 |
| | firm | 5 |
| | too firm | 6 |
| Dough Extensibility: | too short | 1 |
| | short | 2 |
| | normal | 3 |
| | good | 4 |
| | long | 5 |
| | too long | 6 |

Dough stability/Shock test: After the second proof a pan containing the dough is dropped from a height of 20 cm. The dough is baked and the volume of the resulting bread is determined.

Gluten Strengthening: The strengthening effect of a given dough conditioner on heat flour dough or gluten dough may be measured by dynamic Theological measurements. These measurements are able to show the strength of a dough under oscillation. Both wheat flour dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ (Delta). An increase in the storage modulus G' and a decrease in the phase angle δ indicate a stronger and more elastic dough.

Example 1

Fermentation and Mycelial Tissue Preparation

*Fusarium venenatum* CC1-3, a morphological mutant of Fusarium strain ATCC 20334 (Wiebe et al., 1991, *Mycol. Research* 95: 1284–1288), was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology,* Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 μg of poly(A)+ mRNA according to the method of Gubler and Hoffinan (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria,* Cold Spring Harbor Press, Cold Spring Harbor, N.Y.) which contained kanamycin at a final concentration of 50 μg/ml.

Two independent directional cDNA libraries were constructed using the plasmid cloning vector pZErO-2. 1.

Library A was made using mRNA from mycelia harvested at four days, and Library B was constructed with mRNA from the six day time point. Neither cDNA library was amplified in order to examine a representative "snapshot" of the gene expression profile in the cells. Instead the libraries were plated, titered, and independent clones from each was analyzed by DNA sequencing.

Library A (4 day cells) consisted about $7.5 \times 10^4$ independent clones and Library B (6 day cells) consisted of roughly $1.2 \times 10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg.=1050 bp). Similarly, 39 of 40 colonies (97.5%) picked from Library B had inserts with sizes ranging from 800 bp to 3600 bp (avg.=1380 bp).

Example 3

Template Preparation and Nucleotide Sequencing

From each cDNA library described in Example 2, 1192 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing was done with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al., 1992, *Journal of Virology Methods* 38: 47–60) and the reverse lac sequencing primer.

Example 4

Analysis of DNA Sequence Data

Nucleotide sequence data were scrutinized for quality, and samples giving improper spacing or ambiguity levels exceeding 2% were discarded or re-run. Vector sequences were removed with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to determine multiplicity using AutoAssembler™ software (Perkin-Elmer Applied Biosystems, Inc., Foster City, Calif.). Lastly, all sequences were translated in three frames and searched against a non-redundant data base (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of Lactonohydrolase cDNA Clone

Putative lactonohydrolase clones were identified by partial sequencing of random cDNA clones using an Applied Biosystems Model 377 XL Automated DNA Sequencer according to the manufacturer's instructions and comparison of the deduced amino acid sequence to the amino acid sequence of *Fusarium oxysporum* lactonohydrolase (Swissprot accession number W21857) as described in Example 4. Among several clones discovered in this manner, one was presumed to be full-length on the basis of its alignment to the *Fusarium oxysporum* lactonohydrolase amino acid sequence and the presence of a possible signal peptide, detected using the Signal-P computer program (Nielsen, et al., 1997, *Protein Engineering* 10: 1–6). This clone designated *E. coli* FA0576, containing pFA0576, was selected for nucleotide sequence analysis and expression studies.

Example 6

Nucleotide Sequencing and Characterization of the *Fusarium venenatum* Lactonohydrolase cDNA from *E. coli* FA0576

DNA sequencing was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.). The lactonohydrolase clone from *E. coli* FA0576 was sequenced to an average redundancy of 5.9.

The lactonohydrolase clone encoded an open reading frame of 1200 bp encoding a polypeptide of 400 amino acids. The nucleotide sequence (SEQ ID NO. 1) and deduced amino acid sequence (SEQ ID NO. 2) are shown in FIG. 1. Using the SignalP program (Nielsen et al., 1997, *Protein Engineering* 10: 1–6), a signal peptide of 17 residues was predicted. Thus, the mature lactonohydrolase is composed of 383 amino acids.

A comparative alignment of lactonohydrolase sequences was undertaken using the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty= 3, windows=5, and diagonals=5.

The comparative alignment showed that the *Fusarium venenatum* lactonohydrolase shares 87% identity with the lactonohydrolase from *Fusarium oxysporum* (WO 97/10341). There are 5 potential N-linked glycosylation sites (Asn-X-Ser/Thr) within the *Fusarium venenatum* lactonohydrolase, however, one of these sites contains an internal Pro residue, and thus, it is not likely to be utilized. All of the remaining glycosylation sites are conserved in the *Fusarium oxysporum* lactonohydrolase, which is known to bear 3 types of N-linked high-mannose carbohydrates at Asn residues 28, 106, 179, and 277 (WO 97/10341).

Example 7

Construction of pDM181

Plasmid pDM181 was constructed using the technique of splice overlap extension to fuse the 1.2 kb *Fusarium* oxysporum trypsin promoter (SP387) to the 1.1 kb *Fusarium oxysporum* trypsin terminator (SP387). A polylinker containing SwaI, KpnI and PacI restriction sites was inserted between the promoter and terminator as part of the overlapping PCR strategy. At the 5' end of the promoter a XhoI site was added and the native EcoRI site was preserved. At the 3' end of the terminator EcoRI, HindIII and NsiI sites were incorporated by the PCR reaction.

A PCR fragment containing −1208 to −1 of the *Fusarium oxysporum* trypsin promoter plus a 25 base pair polylinker was generated from plasmid pJRoy20 (Royer et al., 1995, *Biotechnology* 13: 1479–1483) using the following primers:

```
Primer 1 (sense) (SEQ ID NO. 3):
5'-GAGCTCGAGGAATTCTTACAAACCTTCAAC-3'
      XhoI   EcoRI Primer 2 (antisense) (SEQ ID NO. 4):
5'-TTAATTAAGGTACCTGAATTTAAATGGTGAAGAGATAGATATCCAAG-3'
    PacI     KpnI      SwaI
```

The 100 µl PCR reaction contained 1×Pwo buffer (Boehringer Mannheim, Indianapolis, Ind.), 200 µM each of dATP, dCTP, dGTP, and dTTP, 10 ng of pJRoy20, and 5 units of Pwo DNA polymerase (Boehringer Mannheim, Indianapolis, Ind.). PCR conditions used were 95° C. for 3 minutes followed by 25 cycles each at 95° C. for 30 seconds, 50° C. for 1 minute, and 72° C. for 1 minute. The final extension cycle was at 72° C. for 5 minutes.

Using the same PCR conditions, a second PCR fragment containing bp −5 to −1 of the *Fusarium oxysporum* trypsin promoter, a 25 base pair polylinker, and 1060 base pairs of the 3' untranslated region of the *Fusarium oxysporum* trypsin gene (terminator region) was generated from plasmid pJRoy20 using the following primers:

```
Primer 3 (sense) (SEQ ID NO. 5):
5'-TCACCATTTAAATTCAGGTACCTTAATTAAATTCCTTGTTGGAAGCGTCGA-3'
         SwaI      KpnI     PacI Primer 4 (antisense) (SEQ ID NO. 6):
5'-TGGTATGCATAAGCTTGAATTCAGGTAAACAAGATATAATTT-3'
      NsiI HindIII  EcoRI
```

The final 2.3 kb overlapping PCR fragment which contained −1208 to −1 of the *Fusarium oxysporum* trypsin promoter, the 25 base pair polylinker and 1060 base pairs of the *Fusarium oxysporum* trypsin terminator was obtained using 0.2 µl of the first PCR (promoter) reaction and 3 µl of the second (terminator) reaction as templated and primers 1 and 4. The PCR conditions used were 95° C. for 3 minutes followed by 30 cycles each at 95° C. for 30 seconds, 62° C. for 1 minute, and 72° C. for 3 minutes. The final extension cycle was at 72° C. for 5 minutes. Pwo DNA polymerase was also used for this reaction.

The resulting 2.3 kb fragment containing the trypsin promoter, the polylinker, and the trypsin terminator was digested with EcoRI and ligated into the EcoRI digested vector pMT1612 containing the bar gene (WO 97/26330) to create pDM181 (FIG. 2).

Example 8

Construction of Plasmid pSheB1

Figure 3:
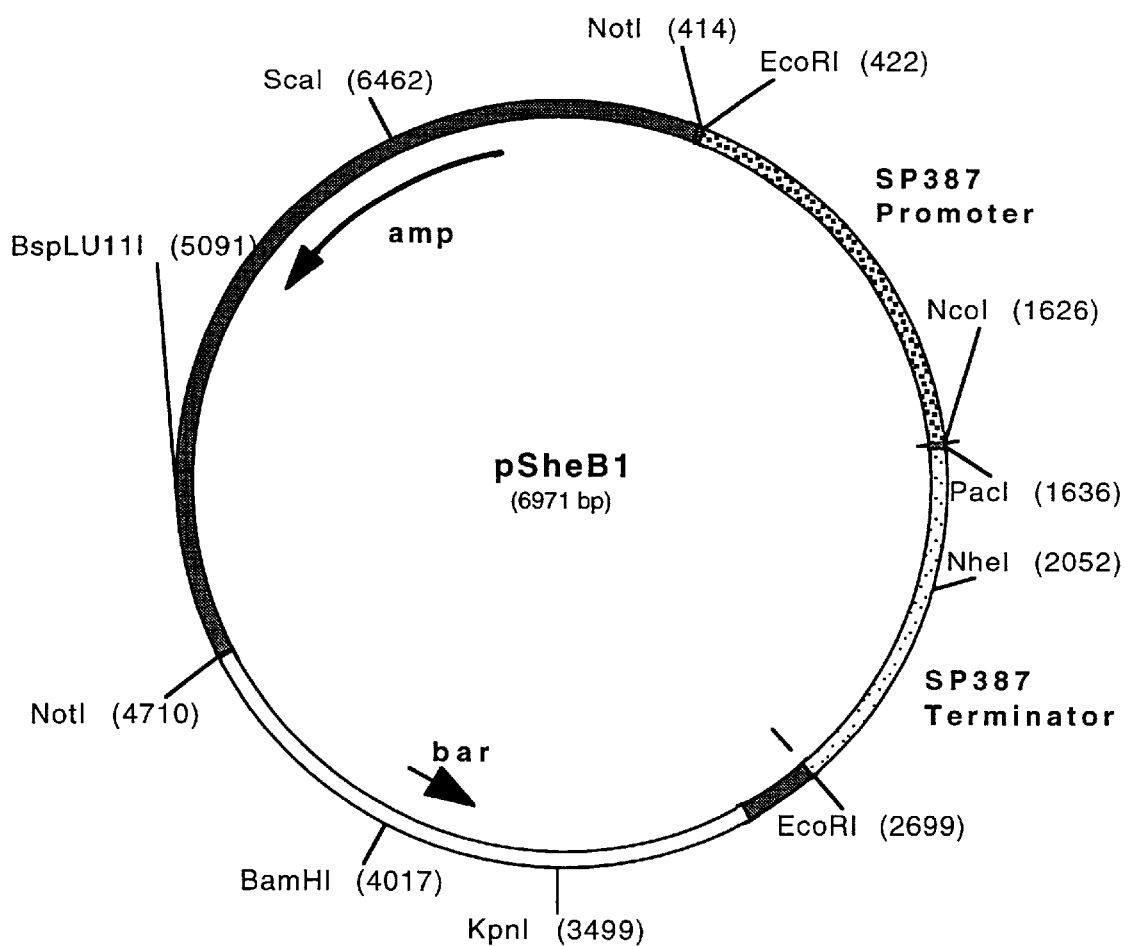
FIG. 3 shows a restriction map of pSheB1.

The *Fusarium venenatum* expression vector pSheB1 (FIG. 3) was generated by modification of pDM181. The modifications included (a) removal of two NcoI sites within the pDM181 sequence, and (b) restoration of the natural translation start of the *Fusarium oxysporum* trypsin promoter (reconstruction of an NcoI site at the ATG start codon).

Removal of two NcoI sites within the pDM181 sequence was accomplished using the QuikChange™ site-directed mutagenesis kit (Stratagene Cloning Systems, La Jolla, Calif.) according to the manufacturer's instruction with the following pairs of mutagenesis primers:

5'-dCAGTGAATTGGCCTCGATGGCCGCGGCCGCGA ATT-3' plus (SEQ ID NO. 7)

5'-dAATTCGCGGCCGCGGCCATCGAGGCCAATTC ACTG-3' (SEQ ID NO. 8)

5'-dCACGAAGGAAAGACGATGGCTTTCACGGTGT CTG-3' plus (SEQ ID NO. 9)

5'-dCAGACACCGTGAAAGCCATCGTCTTTCCTTC GTG-3' (SEQ ID NO. 10)

Restoration of the natural translation start of the *Fusarium oxysporum* trypsin promoter was also accomplished using the Stratagene QuikChange™ site directed mutagenesis kit in conjunction with the following pair of mutagenesis primers:

5'-dCTATCTCTTCACCATGGTACCTTAATTAAATAC CTTGTTGGAAGCG-3' plus (SEQ ID NO. 11)

5'-dCGCTTCCAACAAGGTATTTAATTAAGGTACCA TGGTGAAGAGATAG-3' (SEQ ID NO. 12)

All site-directed changes were confirmed by DNA sequence analysis of the appropriate vector regions.

Example 9

Construction of Expression Vector pTriggs1

The lactonohydrolase-expression vector pTriggs1 (FIG. 4) using the following protocol. The lactonohydrolase coding region was amplified from clone FA0576 using the following pair of primers:

5'-dCGGCATGCCTTCCACCATTGCTG-3' (forward) (SEQ ID NO. 13)

5'-dTTAATTAACTAGTCATATAACTTGGGTCC-3' (reverse) (SEQ ID NO. 14).

The forward primer introduces an SphI restriction site at the start codon, and the reverse primer introduces a PacI site after the stop codon.

The amplification reaction (50 µl) contained the following components: 0.8 µg of clone FA0576 cDNA, 40 pmol of the forward primer, 40 pmol of the reverse primer, 200 µM each of dATP, dCTP, dGTP, and dTTP, 1×Pwo DNA polymerase buffer, and 2.5 units of Pwo DNA polymerase. The reactions were incubated in a Perkin-Elmer Model 480 Thermal Cycler programmed for 30 cycles each at 95° C. for 3 minutes, 58° C. for 2 minutes, and 72° C. for 2 minutes. The reaction products were isolated on a 1.5% agarose gel (Eastman Kodak, Rochester, N.Y.) where a 1.2 kb product band was excised from the gel and purified using Qiaex II (Qiagen, Chatsworth, Calif.) according to the manufacturer's instructions.

The amplified lactonohydrolase segment was digested with SphI and then treated with DNA polymerase I (Klenow fragment; Boehringer Mannheim, Indianapolis, Ind.) in the presence of dNTPs. The 3→5' exonuclease activity of this enzyme removes the 4 nucleotides of the SphI cohesive end, generating a blunt-ended DNA fragment. The Klenow-treated fragment was then digested with PacI and purified by agarose gel electrophoresis using standard methods (see Sambrook et al., 1989, supra).

Figure 4:
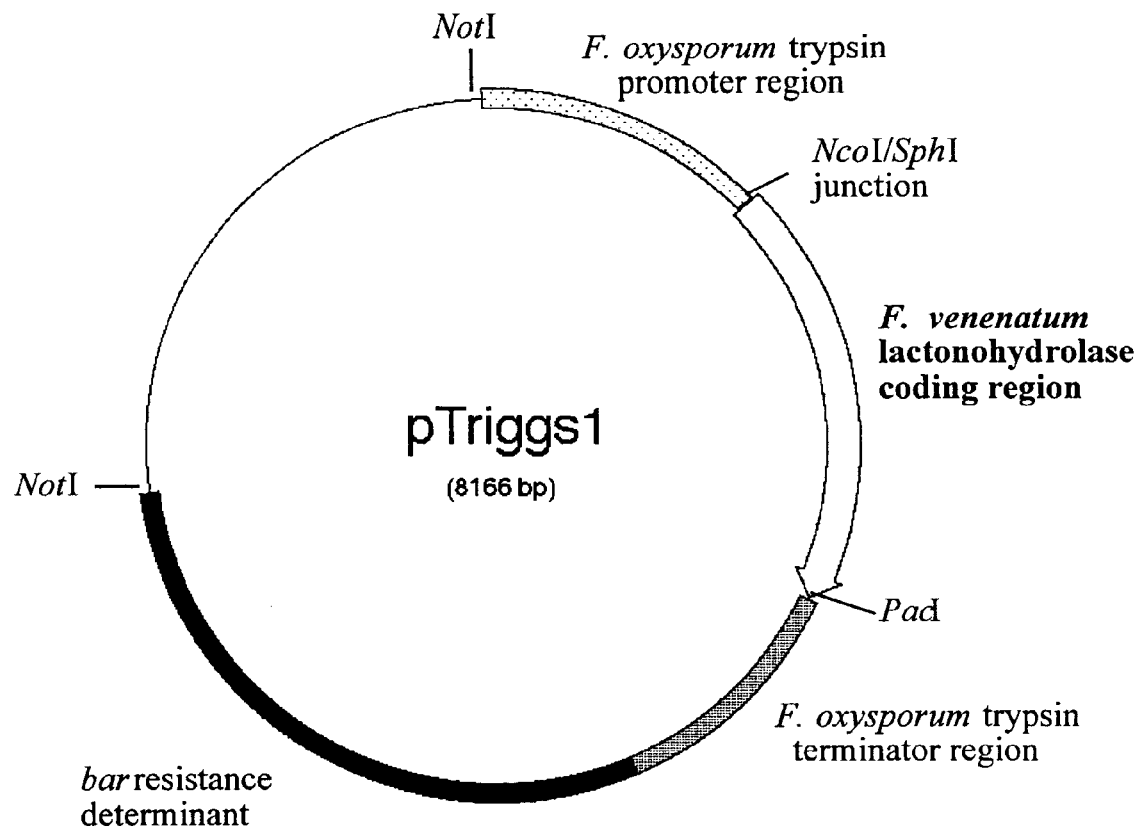
FIG. 4 shows a restriction map of pTriggs1.

The purified DNA segment was ligated to the vector pSheB 1 which had been previously cleaved with NcoI, treated with DNA polymerase I (Klenow fragment) as above, then digested with PacI. Treating the NcoI-digested vector with Klenow fragment results in "filling-in" of the NcoI cohesive end, thereby making it blunt and compatible with the Klenow-treated SphI site of the lactonohydrolase DNA segment. The resulting expression plasmid was designated pTriggsl (FIG. 4).

Example 10

Expression of Lactonohydrolase cDNA in *Fusarium venenatum*

Spores of *Fusarium venenatum* CC1-3 (MLY-3) were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4 \times 10^7$ spores of *Fusarium venenatum* CC1-3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvxrd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25 \times 10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* CC1-3 were thawed on ice. Five pg of pTriggs1 described in Example 9 and 5 μl of heparin (5 mg per ml of STC) was added to a 50 ml sterile polypropylene tube. One hundred μl of protoplasts was added, mixed gently, and incubated on ice for 30 minutes. One ml of SPTC was added and incubated 20 minutes at room temperature. After the addition of 25 ml of 40° C. COVE top agarose, the mixture was poured onto an empty 150 mm diameter plate and incubated overnight at room temperature. Then an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Three transformants were picked directly from the selection plates (COVE underlay with COVE-BASTA™ overlay) into 125 ml shake flasks containing 25 ml of M400Da medium supplemented with 1 mM $CaCl_2$ and 100 μg/ml ampicillin (to prevent bacterial contamination) and incubated at 28° C., 200 rpm on a platform shaker for 6 days. The untransformed recipient strain was also included as a negative control.

Flasks were sampled at 6 days. Cells were removed by centrifugation, and 10 μl of each supernatant sample was heated to 95° C. for 5 minutes with an equal volume of SDS-PAGE sample buffer (Novex Experimental Technology, San Diego, Calif.). The denatured supernatant proteins were separated on a 10–20% gradient gel (Novex Experimental Technology, San Diego, Calif.) and stained with Coomassie blue.

SDS-PAGE analysis showed that the lactonohydrolase-producing transformants secrete a prominent polypeptide with an apparent molecular weight of approximately 55 kDa. The apparent molecular weight of this species (ca. 55,000) is substantially greater than the predicted molecular weight of the mature lactonohydrolase (ca. 41,600), suggesting that the enzyme may be extensively glycosylated. The observed molecular weight agrees closely to the subunit molecular weight of the *Fusarium oxysporum* lactonohydrolase (60,000) reported by Shimizu and Kataoka (1996, *Annals of the New York Academy of Sciences* 799: 650–658). Active lactonohydrolase is reportedly a dimer (Shimizu and Kataoka, 1996, supra).

Example 11

Purification of Recombinant Lactonohydrolase

The recombinant lactonohydrolase prepared as described in Example 10 was filtered through Miracloth. The filtrate was then centrifuged, and the resulting supernatant was filtered through a 0.45 μm filter. The filtered sample had a volume of 64 ml, which was diluted to 360 ml using 20 mM Tris-HCl pH 7.45 containing 1 mM CaCl $_2$. The diluted sample had a pH of 7.76 and a conductivity of 2.76 mS.

The sample then was loaded onto XK26 column containing 64 ml of Q-Sepharose Big Beads. The column had been pre-equilibrated with 400 ml of 20 mM Tris-HCl pH 7.45 containing 1 mM $CaCl_2$. After loading the sample, the column was washed with 20 mM Tris-HCl pH 7.45, containing 1 mM $CaCl_2$ until baseline was reached. The enzyme was then eluted using a salt gradient from 0–0.4 M NaCl in 20 mM Tris-HCl pH 7.45 at a flow rate of 5 ml per minute over 7.8 column volumes. The enzyme eluted at ~0.15 M NaCl. The fractions were assayed for lactonohydrolase activity according to the following protocol.

Lactonohydrolase activity was measured by adding 20 μl of a diluted enzyme sample to 40 μl of 100 mM galactonolactone and 140 μl of 50 mM potassium phosphate pH 7, mixing on ice, and incubating the mixture at 30° C. for 15 minutes. The reaction was stopped by placing on ice. Then, 200 μl of cold alkaline hydroxylamine (equal volumes of 2 N hydroxylamine-HCl and 3.5 N sodium hydroxide) was added to the sample on ice; followed by 400 μl of ethanolic ferric chloride (equal volumes of 10% w/v ferric chloride in 4 N HCl and 95% ethanol) to achieve color development. The absorbance of a 200 μl aliquot was measured at 520 nm in a 96-well plate with a Molecular Devices Thermomax Microplate Reader.

Fractions with lactonohydrolase activity were then analyzed by SDS-PAGE. The enzyme was found to be greater than 95% homogenous by SDS-PAGE in the fractions. The fractions were then pooled.

The purified lactonohydrolase was concentrated from 0.7 to 2.3 mg/ml using an Centricon® concentrator (Amicon, Inc., Beverly, Mass.). The filtrate from the concentration was used in the control for the baking test described in Example 12.

Example 12

Baking with Lactonohydrolase

The "Basic White" breads were made in two Welbilt bread machines according to Table 1.

TABLE 1

Basic White bread

| | |
|---|---|
| Dough: | Distilled H$_2$O, 184 g; baking enzymes; Crisco vegetable oil, 21 ml; Carnation nonfat dry milk, 9.3 g; salt, 7.4 g; sugar, 23 g; Robin Hood flour, 339 g; Fleischmann yeast, 5.9 g. (Add the ingredients in sequence) |
| Protocol: | Mix (first kneading) for 15 minutes<br>Rise (first) for 32 minutes<br>Mix (second kneading) for 23 minutes<br>Rise (second) for 20 minutes<br>Punch down for 2 seconds<br>Rise (third) for 65 minutes<br>Bake for 55 minutes (all steps automated in a Welbilt bread machine) |

The baking enzymes were dosed at 10 ppm for the lactonohydrolase, 1000 ppm for GLUZYME™ 500 MG (along with 5000 ppm D-glucose), and/or 600 ppm for NOVOZYM™ 906. A control without enzyme was also run. The volume of the breads was measured by sand displacement. GLUZYME™ 500 MG and NOVOZYM® 906 are available form Novo Nordisk A/S, Bagsvwrd, Denmark. NOVOZYM® 906 is an enzyme preparation containing FUNGAMYL® and GLUZYME™. The baked breads had weights of 520–530 g and volumes in the range of 0.7–1.5 1.

The results showed that the inclusion of the lactonohydrolase in the dough alone made the dough stronger. The resulting bread had a rough crust appearance, indicating difficulty for the machine to mix the dough. Compared to the control, the bread had an 11% reduction in volume.

GLUZYME™ 500 MG alone (added along with glucose) resulted in a bread with significantly reduced volume (50%) and a very rough crust, indicating the negative rheological effect of the glucose oxidase on dough.

The inclusion of GLUZYME™ 500 MG and the lactonohydrolase resulted in a bread with similar volume (+1%) and crust appearance.

NOVOZYM® 906 added in combination with lactonohydrolase resulted in bread with a larger volume (8–11%), more evenly distributed gas cells, spongier texture, and smoother crust. There appeared to be a desirable synergy among the three enzymes, lactonohydrolase, GLUZYME™, and FUNGAMYL®, for producing better bread.

Example 13

Baking Trials with Lactonohydrolase

The effect of lactonohydrolase on doughs containing ascorbic acid (a chemical oxidant) was investigated using the protocol for white bread (I).

When 10 ppm lactonohydrolase was added to a dough containing 60 ppm ascorbic acid, a 1% increase of the loaf volume was observed for the baked breads.

When 0.25% glucano-Δ-lactone (GDL) was included in the dough containing 60 ppm ascorbic acid, a 1% increase of the loaf volume was observed. When 10 ppm lactonohydrolase was added, an additional 1% increase of the loaf volume was observed.

When 150 Fungal-Xylanase-Unit (FXU) of PENTOPAN™ MONO was included per kg of dough containing 60 ppm ascorbic acid, a 16% increase of the loaf volume was observed. When 10 ppm lactonohydrolase was added to the dough, the volume increase was reduced to 4%.

The effect of lactonohydrolase on doughs containing glucose oxidase and fungal alpha-amylase was also investigated using the same protocol described above.

When 200 glucose oxidase units (GODU) (or1.4 ppm) of GLUZYME™, and 50 Fungal-Amylase Units (FAU) of FUNGAMYL® per kg of dough were included, a 6% increase of the loaf volume was observed for the baked breads. When 5 ppm lactonohydrolase was added per kg of dough, an additional 6% increase of the loaf volume was observed.

When 200 GODU of GLUZYME™ per kg, 50 FAU of FUNGAMYL® per kg, and 120 FXU of PENTOPAN™ MONO per kg were included into the dough, an 18% increase of the loaf volume was observed for the baked breads. When 5 ppm lactonohydrolase was added, an additional 4% increase of the loaf volume was observed.

When 200 GODU of GLUZYME™, 50 FAU of FUNGAMYL®, and 0.25% GDL per kg of dough were included, a 4% increase of the loaf volume was observed for the baked breads. When 5 ppm lactonohydrolase was added to the dough, the volume increase was reduced to 1%.

The results described above demonstrated that lactonohydrolase affected the loaf volume of the bread.

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli TOP10 (pFA0576) | NRRL B-30074 | Oct. 27, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended any of claims.

Various references are cited herein, the disclosures of which are incorporated by reference in their entireties.

What is claimed is:

1. A method for preparing a dough, comprising incorporating into the dough one or more lactonohydrolases, each in the amount of about 0.01 mg to about 100 mg per kilogram of dough for improving one or more properties of the dough and/or a baked product obtained from the dough, wherein the one or more properties are selected from the group consisting of strength of the dough, stability of the dough, stickiness of the dough, machinability of the dough, volume of the baked product, crumb structure of the baked product, softness of the baked product, flavor of the baked product, and antistaling of the baked product.

2. The method of claim 1, wherein the one or more lactonohydrolases are selected from the group consisting of an L-arabinonolactonase (E.C. 3.1.1.15), D-gluconolactonase (E.C. 3.1.1.17), D-glucuronolactonase (E.C. 3.1.1.19), 3-oxoadipate enol-lactonase (E.C. 3.1.1.24), 1,4-lactonase (E.C. 3.1.1.25), D-arabinolactonase (E.C. 3.1.1.30), and 6-phosphogluconolactonase (E.C. 3.1.1.31).

3. The method of claim 1, wherein the amount of the one or more lactonohydrolases is about 0.1 mg to about 25 mg per kilogram of dough.

4. The method of claim 3, wherein the amount of the one or more lactonohydrolases is about 0.5 mg to about 5 mg per kilogram of dough.

5. The method of claim 4, wherein the amount of the one or more lactonohydrolases is about 1 mg to about 5 mg per kilogram of dough.

6. The method of claim 1, wherein the dough is obtained from one or more ingredients selected from the group consisting of wheat meal, wheat flour, corn meal, corn flour, durum flour, rye meal, rye flour, oat meal, oat flour, soy meal, soy flour, sorghum meal, sorghum flour, potato meal, and potato flour.

7. The method of claim 1, wherein the baked product is a bread, roll, French baguette-type bread, pasta, pita bread, tortilla, taco, cake, pancake, biscuit, cookie, pie crust, steamed bread, or crisp bread.

8. The method of claim 1, further comprising incorporating one or more additional enzymes selected from the group consisting of an amylase, cellulase, cyclodextrin glucanotransferase, glycosyltransferase, hemicellulase, laccase, lipase, oxidase, pentosanase, peptidase, peroxidase, phospholipase, protease, protein disulfide isomerase, and transglutaminase.

9. The method of claim 1, further comprising incorporating one or more baking agents selected from the group consisting of a protein, emulsifier, granulated fat, oxidant, amino acid, sugar, salt, flour, and starch.

10. A dough obtained by the method of claim 1.

11. A method for preparing a baked product, comprising baking a dough obtained by the method of claim 1 to produce a baked product.

12. The method of claim 11, wherein the one or more lactonohydrolases improve one or more properties of the baked product selected from the group consisting of volume of the baked product, crumb structure of the baked product, softness of the baked product, flavor of the baked product, and antistaling of the baked product.

13. A baked product obtained by the method of claim 11.

14. A composition for improving one or more properties of a dough and/or a baked product obtained from the dough, comprising one or more lactonohydrolases and one or more added baking agents selected from the group consisting of a protein, emulsifier, granulated fat, oxidant, amino acid, sugar, salt, flour, and starch, wherein the amount of the lactonohydrolase incorporated into the dough is about 0.01 mg to about 100 mg per kilogram of dough, and wherein the one or more improved properties are selected from the group consisting of strength of the dough, stability of the dough, stickiness of the dough, machinability of the dough, volume of the baked product, crumb structure of the baked product, softness of the baked product, flavor of the baked product, and antistaling of the baked product.

15. The composition of claim 14, wherein the one or more lactonohydrolases are selected from the group consisting of an L-arabinonolactonase (E.C. 3.1.1.15), D-gluconolactonase (E.C. 3.1.1.17), D-glucuronolactonase (E.C. 3.1.1.19), 3-oxoadipate enol-lactonase (E.C. 3.1.1.24), 1,4-lactonase (E.C. 3.1.1.25), D-arabinolactonase (E.C. 3.1.1.30), and 6-phosphogluconolactonase (E.C. 3.1.1.31).

16. The composition of claim 14, wherein the composition further comprises one or more additional enzymes selected from the group consisting of an amylase, cellulase, cyclodextrin glucanotransferase, glycosyltransferase, hemicellulase, laccase, lipase, oxidase, pentosanase, peptidase, peroxidase, phospholipase, protease, protein disulfide isomerase, and transglutaminase.

17. The composition of claim 14, wherein the composition further comprises one or more baking agents selected from the group consisting of a protein, emulsifier, granulated fat, oxidant, amino acid, sugar, salt, flour, and starch.

18. A pre-mix for a dough comprising flour one or more lactonohydrolases for improving one or more properties of a dough and/or a baked product obtained from the dough and a baking agent selected from the group consisting of a protein, emulsifier, granulated fat, oxidant, amino acid, sugar, salt, and starch, wherein the one or more lactonohydrolases are incorporated into the dough in the amount of about 0.01 mg to about 100 mg per kilogram of dough, and wherein the one or more improved properties are selected from the group consisting of strength of the dough, stability of the dough, stickiness of the dough, machinability of the dough, volume of the baked product, crumb structure of the baked product, softness of the baked product, flavor of the baked product, and antistaling of the baked product.

19. A baking additive in the form of a granulate or agglomerated powder for improving one or more properties of a dough and/or a baked product obtained from the dough, the additive comprising one or more lactonohydrolases and one or more baking agents selected from the group consisting of a protein, emulsifier, granulated fat, oxidant, amino acid, sugar, salt, flour, and starch, wherein the one or more improved properties are selected from the group consisting of strength of the dough, stability of the dough, stickiness of the dough, machinability of the dough, volume of the baked product, crumb structure of the baked product, softness of the baked product, flavor of the baked product, and antistaling of the baked product.

20. The baking additive of claim 19, wherein more than 95% by weight of the baking additive has a particle size between about 25 and about 500 µm.

* * * * *

SEQUENCE LISTING

<160> NUMBER OF SEQ ID NOS: 14

<210> SEQ ID NO 1
<211> LENGTH: 1334
<212> TYPE: DNA
<213> ORGANISM: Fusarium

<400> SEQUENCE: 1

```
ctcccacacc actcagtttc acttctacct cattcgccat gccttccacc attgctgccc      60
ttgttgtcgg gatttgtggc gttgccgctg ccaaacttcc ctccacggct caggtcattg     120
atcagaagtc tttcaatgtt ttgaaggatg tcccaccacc ttccgtggct aatgacacac     180
tggtctttac atggcccgga gtgacagagg aatctctcgt cgagaaaccc ttccatgttt     240
atgatgatga attcctcgat gtcatcggaa aggatccctc tctgacactt gttgctacgt     300
cagaaagcga ccccatcttc cacgaggctg tagtctggta cccacctaca gacgaggttt     360
ttttcgtgca aaatgcgggt gctcctgcgg caggcactgg cctgaacaag tcttccatca     420
tccagaagat ttctctcaaa gatgcagagg ctttgcgcaa gggaaccctc ggcaaggatg     480
aagtgaaggt gacagtcgtt gacacagcta accctcaagt cattaacccc aatggtggca     540
tttactacaa gggcgaaatc atctttgctg gtgaaggcca aggtgacgaa gttccctcgg     600
cccctttaccg catgaacccc ttgcctccat acaacacaag caccctcctc aacaactact     660
ttggccgcca gttcaactcc ttgaacgacg ttggcatcaa ccccaggaat ggtgacttgt     720
acttcaccga cactctctac ggctatctcc aagacttccg tcctgtccct ggtctgcgaa     780
accaagtgta ccgatacaac ttcgacactg gtgctgtaac tgttgtcgct gatgacttta     840
ctcttcccaa cggtattggt tttgctcctg atggaaagcg tgtctatgtc accgacactg     900
gcatcgctct tggcttctac ggccgtaacc tttcctcccc cgcctctgtt tactctttcg     960
acgtgaacaa ggatggtacc cttgagaacc gcaagacttt tgcctacgta gcttctttca    1020
tcccagacgg tgttcatacc gattccaagg gtcgtgtcta tgctggttgt ggtgacggtg    1080
tccatgtctg gaaccctct ggcaagctca ttggcaagat ctataccggg atcactgctg    1140
ccaacttcca atttgctgga aaaggaagat tgattatcac tggtcagact aagctgttct    1200
acgttaccct ggctgcttca ggacccaagt tatatgacta gaactcccct gtggcagtat    1260
agaaacagat attttaccgt attgatagaa gataatatta attattaatc gataaaaaaa    1320
aaaaaaaaaa aaaa                                                       1334
```

<210> SEQ ID NO 2
<211> LENGTH: 400
<212> TYPE: PRT
<213> ORGANISM: Fusarium

-continued

```
<400> SEQUENCE: 2

Met Pro Ser Thr Ile Ala Ala Leu Val Val Gly Ile Cys Gly Val Ala
  1               5                  10                  15

Ala Ala Lys Leu Pro Ser Thr Ala Gln Val Ile Asp Gln Lys Ser Phe
             20                  25                  30

Asn Val Leu Lys Asp Val Pro Pro Ser Val Ala Asn Asp Thr Leu
         35                  40                  45

Val Phe Thr Trp Pro Gly Val Thr Glu Glu Ser Leu Val Glu Lys Pro
 50                  55                  60

Phe His Val Tyr Asp Asp Glu Phe Leu Asp Val Ile Gly Lys Asp Pro
 65                  70                  75                  80

Ser Leu Thr Leu Val Ala Thr Ser Glu Ser Asp Pro Ile Phe His Glu
                 85                  90                  95

Ala Val Val Trp Tyr Pro Pro Thr Asp Glu Val Phe Phe Val Gln Asn
                100                 105                 110

Ala Gly Ala Pro Ala Ala Gly Thr Gly Leu Asn Lys Ser Ser Ile Ile
            115                 120                 125

Gln Lys Ile Ser Leu Lys Asp Ala Glu Ala Leu Arg Lys Gly Thr Leu
130                 135                 140

Gly Lys Asp Glu Lys Val Thr Val Val Asp Thr Ala Asn Pro Gln
145                 150                 155                 160

Val Ile Asn Pro Asn Gly Gly Ile Tyr Tyr Lys Gly Glu Ile Ile Phe
                165                 170                 175

Ala Gly Glu Gly Gln Gly Asp Glu Val Pro Ser Ala Leu Tyr Arg Met
            180                 185                 190

Asn Pro Leu Pro Pro Tyr Asn Thr Ser Thr Leu Leu Asn Asn Tyr Phe
        195                 200                 205

Gly Arg Gln Phe Asn Ser Leu Asn Asp Val Gly Ile Asn Pro Arg Asn
    210                 215                 220

Gly Asp Leu Tyr Phe Thr Asp Thr Leu Tyr Gly Tyr Leu Gln Asp Phe
225                 230                 235                 240

Arg Pro Val Pro Gly Leu Arg Asn Gln Val Tyr Arg Tyr Asn Phe Asp
                245                 250                 255

Thr Gly Ala Val Thr Val Val Ala Asp Asp Phe Thr Leu Pro Asn Gly
            260                 265                 270

Ile Gly Phe Ala Pro Asp Gly Lys Arg Val Tyr Val Thr Asp Thr Gly
        275                 280                 285

Ile Ala Leu Gly Phe Tyr Gly Arg Asn Leu Ser Ser Pro Ala Ser Val
    290                 295                 300

Tyr Ser Phe Asp Val Asn Lys Asp Gly Thr Leu Glu Asn Arg Lys Thr
305                 310                 315                 320

Phe Ala Tyr Val Ala Ser Phe Ile Pro Asp Gly Val His Thr Asp Ser
                325                 330                 335

Lys Gly Arg Val Tyr Ala Gly Cys Gly Asp Gly Val His Val Trp Asn
            340                 345                 350

Pro Ser Gly Lys Leu Ile Gly Lys Ile Tyr Thr Gly Ile Thr Ala Ala
        355                 360                 365

Asn Phe Gln Phe Ala Gly Lys Gly Arg Leu Ile Ile Thr Gly Gln Thr
    370                 375                 380

Lys Leu Phe Tyr Val Thr Leu Ala Ala Ser Gly Pro Lys Leu Tyr Asp
385                 390                 395                 400
```

<210> SEQ ID NO 3
<211> LENGTH: 30
<212> TYPE: DNA
<213> ORGANISM: Fusarium

<400> SEQUENCE: 3
gagctcgagg aattcttaca aaccttcaac                                30

<210> SEQ ID NO 4
<211> LENGTH: 47
<212> TYPE: DNA
<213> ORGANISM: Fusarium

<400> SEQUENCE: 4
ttaattaagg tacctgaatt taaatggtga agagatagat atccaag              47

<210> SEQ ID NO 5
<211> LENGTH: 51
<212> TYPE: DNA
<213> ORGANISM: Fusarium

<400> SEQUENCE: 5
tcaccattta aattcaggta ccttaattaa attccttgtt ggaagcgtcg a         51

<210> SEQ ID NO 6
<211> LENGTH: 42
<212> TYPE: DNA
<213> ORGANISM: Fusarium

<400> SEQUENCE: 6
tggtatgcat aagcttgaat tcaggtaaac aagatataat tt                   42

<210> SEQ ID NO 7
<211> LENGTH: 35
<212> TYPE: DNA
<213> ORGANISM: Fusarium

<400> SEQUENCE: 7
cagtgaattg gcctcgatgg ccgcggccgc gaatt                           35

<210> SEQ ID NO 8
<211> LENGTH: 35
<212> TYPE: DNA
<213> ORGANISM: Fusarium

<400> SEQUENCE: 8
aattcgcggc cgcggccatc gaggccaatt cactg                           35

<210> SEQ ID NO 9
<211> LENGTH: 34
<212> TYPE: DNA
<213> ORGANISM: Fusarium

<400> SEQUENCE: 9
cacgaaggaa agacgatggc tttcacggtg tctg                            34

<210> SEQ ID NO 10
<211> LENGTH: 34
<212> TYPE: DNA
<213> ORGANISM: Fusarium

<400> SEQUENCE: 10
cagacaccgt gaaagccatc gtctttcctt cgtg                            34

```
<210> SEQ ID NO 11
<211> LENGTH: 46
<212> TYPE: DNA
<213> ORGANISM: Fusarium

<400> SEQUENCE: 11
ctatctcttc accatggtac cttaattaaa taccttgttg gaagcg            46

<210> SEQ ID NO 12
<211> LENGTH: 46
<212> TYPE: DNA
<213> ORGANISM: Fusarium

<400> SEQUENCE: 12
cgcttccaac aaggtattta attaaggtac catggtgaag agatag            46

<210> SEQ ID NO 13
<211> LENGTH: 23
<212> TYPE: DNA
<213> ORGANISM: Fusarium

<400> SEQUENCE: 13
cggcatgcct tccaccattg ctg                                     23

<210> SEQ ID NO 14
<211> LENGTH: 29
<212> TYPE: DNA
<213> ORGANISM: Fusarium

<400> SEQUENCE: 14
ttaattaact agtcatataa cttgggtcc                               29
```